United States Patent [19]

Curran et al.

[11] 4,454,336

[45] Jun. 12, 1984

[54] DERIVATIVES OF 3-(FORMYLMETHYLTHIO)-PROPANOATE

[75] Inventors: William V. Curran, Pearl River; Martin L. Sassiver, Monsey, both of N.Y.; James H. Boothe, Montvale, N.J.

[73] Assignee: American Cyanamid Company, Stamford, Conn.

[21] Appl. No.: 424,825

[22] Filed: Sep. 27, 1982

[51] Int. Cl.$^3$ .................. C07C 147/06; C07C 149/20; C07C 149/437; C07D 285/06
[52] U.S. Cl. ...................................... 560/13; 560/148; 560/153; 548/127
[58] Field of Search .......................... 560/13, 148, 153

[56] References Cited

U.S. PATENT DOCUMENTS 3,115,515  12/1963  Gaul et al. ........................... 560/153

OTHER PUBLICATIONS

*Journal of Heterocyclic Chemistry*, vol. 15, p. 1295, (1978); Demaree et al.
*Journal of Medicinal Chemistry*, vol. 22, No. 10, p. 1214, (1979); Lewis et al.

*Primary Examiner*—Natalie Trousof
*Assistant Examiner*—Patricia M. Scott
*Attorney, Agent, or Firm*—Mary-Ellen M. Timbers

[57] ABSTRACT

This disclosure describes a novel process for the synthesis of 5-mercapto-1,2,3-thiadiazoles which are useful as intermediates in the preparation of antibacterial agents.

1 Claim, No Drawings

DERIVATIVES OF 3-(FORMYLMETHYLTHIO)-PROPANOATE

BRIEF SUMMARY OF THE INVENTION

This invention relates to a novel method for the preparation of 5-mercapto-1,2,3-thiadiazoles and, more particularly, is concerned with a synthetic process as set forth by the following reaction scheme:

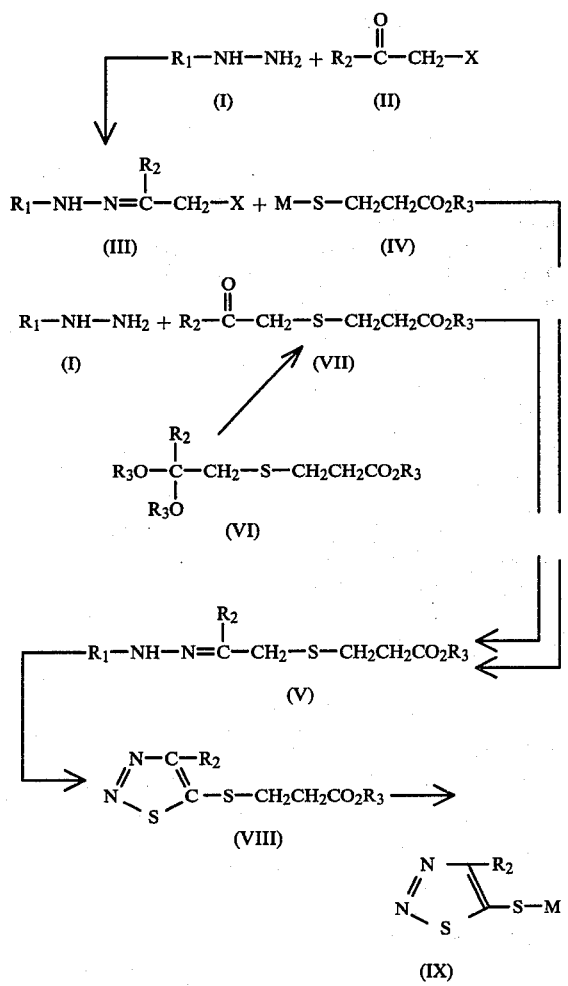

wherein $R_1$ is para-toluenesulfonyl, carbamoyl or carboalkoxy having from two to four carbon atoms; $R_2$ is hydrogen or methyl; $R_3$ is alkyl having up to three carbon atoms; X is chloro, bromo or iodo; and M is sodium or potassium. In accordance with the above reaction scheme; an appropriately substituted hydrazine (I) is condensed with an appropriately substituted α-haloacetaldehyde (II) to provide the corresponding α-haloacetaldehyde hydrazone (III). This condensation is readily carried out in aqueous solution in the presence of sodium acetate at ambient temperatures for a period of several hours. The hydrazone (III) is then reacted with an alkyl thiopropanoate salt (IV) in a lower alkanol as solvent at the reflux temperature thereof for several hours whereby the corresponding alkyl 3-(formylmethylthio)propanoate hydrazone (V) is obtained.

Alternatively, an alkyl 3-thiopropanoate sodium salt of the formula $Na-S-CH_2CH_2CO_2R_3$ is condensed with a 1,1-dialkoxyethyl bromide of the formula $(R_3O)_2CR_2CH_2Br$ in a solvent such as methanol at the reflux temperature for several hours to provide the corresponding alkyl 3-[(2-dialkoxyethyl)thio]propanoate (VI). Removal of the solvent and extraction into ethyl acetate provides the purified derivative (VI) which is then hydrolyzed in dilute (1%) hydrochloric acid at ambient temperatures to provide the corresponding alkyl 3-[(2-oxoethyl)thio]-propanote (VII). Condensation of (VII) with an appropriately substituted hydrazine (I) under nitrogen for several hours in ethanol at the reflux temperature, followed by extraction in ethyl acetate and purification by column chromatography on silica gel using ethyl acetate:hexane as eluant provides the corresponding alkyl 3-(formylmethylthio)-propanoate hydrazone (V).

Cyclization of (V) is accomplished with thionyl chloride and triethylamine in methylene chloride for a few hours at ambient temperatures. Purification by chromatography on silica gel using the system hexane:ethyl acetate (4:1) provides the corresponding 5-alkoxy carbonylethylthio-1,2,3-thiadiazole (VIII). Treatment of (VIII) with sodium or potassium methoxide in methanol at ambient temperatures for an hour or so followed by precipitation with diethyl ether provides the 5-mercapto-1,2,3-thiadiazole alkali metal salt (IX).

The 5-mercapto-1,2,3-thiadiazole potassium salt is disclosed in J. Heterocyclic Chemistry 15, 1298 (1978). Its utility is disclosed in J. Med. Chem. 22, 1214 (1979) where it is employed to form a derivative of 7-aminocephalosporanic acid having activity as an antibacterial agent. The presently disclosed method provides a means of making the 1,2,3-thiadiazoles in higher yield and by a more convenient method which does not use diazomethane and thiophosgene and also does not give the isomeric 1,3,4-thiadiazole.

The invention will be described in greater detail in conjunction with the following specific examples.

EXAMPLE 1

Methyl 3-(2-diethoxyethylthio)propanoate

A 12.05 g. portion of methyl 3-thiopropanoate is dissolved in 50 ml. of methanol. A 5.4 g. portion of sodium methoxide is added in portions with stirring. A 19.7 g. portion of 1,1-diethoxyethyl bromide is added dropwise, then the solution is refluxed for 3 hours during which time a precipitate forms. The suspension is concentrated in vacuo until the methanol is removed and then the residue is distributed between 50 ml. each of water and ethyl acetate. The aqueous layer is extracted again with ethyl acetate and the combined organic extracts are dried and concentrated to an oily residue which is distilled in vacuo, [b.p. 109°–112° C. (0.6–0.7 mm. Hg.)] giving 12.3 g. of the desired compound.

EXAMPLE 2

Chloroacetaldehyde semicarbazone

A 34.9 g. portion of a 45% aqueous solution of chloroacetaldehyde is diluted with 100 ml. of water and then filtered. The filtrate is added to a solution of 22.2 g. of semicarbazide hydrochloride and 30 g. of sodium acetate trihydrate in 100 ml. of water. The mixture is stirred and then allowed to stand overnight. The solid is collected, washed with water, dried and recrystallized from ethanol giving the desired compound, m.p. 133°–135° C. (dec.).

EXAMPLE 3

Methyl 3-(formylmethylthio)propanoate semicarbazone

A mixture of 1.08 g. of sodium methoxide, 2.4 g. of methylthiopropanoate and 2.72 g. of chloroacetaldehyde semicarbazone in 40 ml. of methanol is stirred and refluxed for 4–5 hours. The mixture is filtered and the filtrate concentrated to an oil which is purified by chromatography on silica gel, giving the desired compound.

EXAMPLE 4

Methyl 3-(formylmethylthio)-propanoate

A mixture of 13.2 g. of methyl 3-[(2-diethoxyethyl)-thio]-propanoate and 200 ml. of 1% hydrochloric acid is stirred, under nitrogen, for 4 hours. The solution is decanted from a small amount of insoluble oil, adjusted to pH 4.5 with sodium acetate and extracted with four 100 ml. portions of ethyl acetate. The combined extracts are dried over magnesium sulfate and then evaporated, giving 8.2 g. of the desired compound as a colorless oil.

EXAMPLE 5

Methyl 3-(formylmethylthio)-propanoate semicarbazone

A mixture of 6.7 g. of semicarbazide hydrochloride and 6.7 g. of sodium acetate in 50 ml. of ethanol is refluxed for 10 minutes, then filtered while hot and 10.6 g. of methyl 3-(formylmethylthio)-propanoate is added to the filtrate. This solution is refluxed for one hour, then cooled and diluted with 200 ml. of water. The mixture is extracted with three 100 ml. of portions of ethyl acetate. The organic extracts are combined, washed with brine, dried over magnesium sulfate and evaporated, giving 11.8 g. of the desired compound as an amber oil.

EXAMPLE 6

Methyl (3-formylmethylthio)propanoate ethoxycarbonylhydrazone

A 100 ml. portion of 1% hydrochloric acid is purged with nitrogen for 10 minutes and then added to 4.73 g. of methyl 3-(2-diethoxyethylthio)propanoate. Nitrogen is bubbled into this mixture for 5 minutes then the flask is stoppered and stirred for 17 hours. The pH of the solution is raised to 4.2 with saturated aqueous sodium acetate and 2.08 g. of ethyl carbazate in 8 ml. of water is added. The solution is briefly flushed with nitrogen, then stoppered and stirred for 2 hours and then extracted with two 100 ml. portions of ethyl acetate. The combined extracts are dried and evaporated to 5.09 g. of an oil. This oil is chromatographed on a 200 g. silica gel column using ethyl acetate:hexane (1:1) as eluant and collecting fractions of 100 ml. each. Fractions 8–13, containing the desired component are combined and evaporated, giving 1.8 g. of an oil which crystallizes on standing.

Certain variations of the above procedure may be used to derive the desired product.

(A) Hydrolysis of 5.9 g. of methyl 3-(2-diethoxyethyl-thio)propanoate is carried out for 3 hours, under nitrogen in 100 ml. of 1% hydrochloric acid. Removal by pipette of a small quantity of undissolved oil, followed by reaction of the solution with 2.6 g. of ethyl carbazate for 2 hours gives, after workup as described above, 6.11 g. of crude product.

(B) The syrup from workup of a 10 mmole run is treated with ether to precipitate some of the undesired lower Rf component and the residue is chromatographed as described above.

EXAMPLE 7

Methyl 3-(formylmethylthio)-propanoate p-toluenesulfonyl hydrazone

A mixture of 8.2 g. of methyl 3-(formylmethylthio)-propanoate and 9.4 g. of p-toluenesulfonylhydrazide in 75 ml. of ethanol is refluxed for 2 hours, then chilled and the desired compound is collected by filtration giving 5.4 g., m.p. 94°–96° C.

EXAMPLE 8

5-Methoxycarbonylethylthio-1,2,3-thiadiazole

A 0.5 g. portion of methyl 3-(formylmethylthio)-propanoate p-toluenesulfonyl hydrazone is added to 4 ml. of thionyl chloride and allowed to react for 30 minutes. The mixture is evaporated to dryness, the residue dissolved in methylene chloride and again evaporated. This crude product is purified by thick layer chromatography giving 184 mg. of the desired compound.

EXAMPLE 9

5-Methoxycarbonylethylthio-1,2,3-thiadiazole

A solution of 2.40 ml. of thionyl chloride in 3 ml. of methylene chloride is added rapidly, dropwise to a stirred solution of 8.23 g. of methyl (3-formylmethylthio)propanoate ethoxycarbonylhydrazone and 9.25 ml. of triethylamine in 25 ml. of methylene chloride. After 30 minutes, 2.4 ml. of thionyl chloride is added rapidly, dropwise. After 60 minutes, 2.4 ml. of thionyl chloride is again added as above. After a total reaction time of 2 hours, the mixture is evaporated at reduced pressure and with mild heat. Ether is added to the residue which is then filtered. The filtrate is evaporated to a residue which is chromatographed on 500 g. of silica gel using hexane:ethyl acetate (4:1) and collecting fractions of 50 ml. each. Fractions 10–21 are collected, pooled and evaporated, giving 3.13 g. of the desired compound as an oil.

It is also possible to perform this reaction with another inert solvent such as toluene or without a solvent. Also, the triethylamine can be omitted and the molar equivalents of thionyl chloride can be reduced, but yields will be less.

EXAMPLE 10

5-Methoxycarbonylethylthio-1,2,3-thiadiazole

A 177.5 g. portion of methyl 3-(formylmethylthio)-propanoate semicarbazone is diluted with 100 ml. of dry methylene chloride and this is added, fairly rapidly, using a dropping funnel, to 875 ml. of thionyl chloride with rapid stirring which is continued for 2 hours after addition is complete. The thionyl chloride is then removed under reduced pressure and two portions of methylene chloride are added and removed under reduced pressure. The residue is dissolved in ethyl acetate, filtered and the filtrate washed first with saturated aqueous sodium bicarbonate and then with brine. The solution is dried over magnesium sulfate, an equal volume of hexane is added and the solution is filtered through a silica gel pad topped with diatomaceous earth. The pad is washed with a 1:1 solution of ethyl acetate and hexane and this wash is concentrated under reduced pressure to an oil. The oil is dissolved in 100 ml.

of a 20% ethyl acetate in hexane solution. One half of this solution is injected onto a Waters Prep 500 HPLC, using two prepacked columns and eluted with a solution of 12.5% ethyl acetate in hexane containing 1% methanol. After 2.5 liters of solvent has been eluted (one liter being the void volume), fractions 3–7 (containing approximately 3 liters of eluent) are combined and concentrated under reduced pressure. This procedure is repeated with the other half of the solution of the product. Total yield is 57.8 g. of the desired compound.

EXAMPLE 11

Sodium 1,2,3-thiadiazole-5-thiolate

A solution of 756 mg. of sodium methoxide in 20 ml. of methanol is added to a solution of 3.13 g. of 5-methoxycarbonylethylthio-1,2,3,-thiadiazole in 30 ml. of methanol. After 45 minutes, the reaction solution is evaporated in vacuo to about 5 ml. A 3 ml. portion of methanol is added and then about 15 ml. of ether causing precipitation of a solid. This solid is collected, washed with ether, dried and recrystallized from methanol-ether, giving 1.94 g. of the desired product.

We claim:

1. A compound having the following formula:

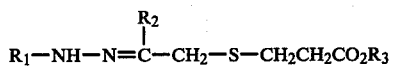

wherein $R_1$ is para-toluenesulfonyl, carbamoyl or carboalkoxy having from two to four carbon atoms, $R_2$ is hydrogen or methyl and $R_3$ is $C_1$–$C_3$ alkyl.

* * * * *